United States Patent

Matsui et al.

[11] 3,984,435
[45] Oct. 5, 1976

[54] HERBICIDAL N-SUBSTITUTED-Δ¹-TETRAHYDROPHTHALIMIDE

[75] Inventors: Kazuo Matsui; Hiroshi Kasugai, both of Tokyo; Kuni Matsuya; Hiroyasu Aizawa, both of Kawasaki, all of Japan

[73] Assignee: Mitsubishi Chemical Industries Ltd., Tokyo, Japan

[22] Filed: Feb. 10, 1975

[21] Appl. No.: 548,396

Related U.S. Application Data

[62] Division of Ser. No. 207,957, Dec. 14, 1971, Pat. No. 3,878,224.

[30] Foreign Application Priority Data

Dec. 23, 1970 Japan.............................. 45-115868
Oct. 14, 1971 Japan.............................. 46-81083
Oct. 18, 1971 Japan.............................. 46-82349
Oct. 26, 1971 Japan.............................. 46-84803

[52] U.S. Cl................................ 260/326 A; 71/96; 260/326 N; 260/326 HL
[51] Int. Cl.²........................................ C07D 209/48
[58] Field of Search ...... 260/326 A, 326 N, 326 HL

[56] References Cited

UNITED STATES PATENTS 3,745,170   7/1973   Fujinami et al. ............. 260/326 HL
3,766,218   10/1973   Ueda et al. .................... 260/326 NS

OTHER PUBLICATIONS

Artico et al., "Biochem. Pharmacol," vol. 17(6), pp. 893–898 (1968) abstracted in Chem. Abstracts, vol. 69, No. 76807P and Chem. Abstracts – Subject Index, vols. 66–75, p. 24160s.

*Primary Examiner*—Lewls Gotts
*Assistant Examiner*—S. P. Williams
*Attorney, Agent, or Firm*—Bierman & Bierman

[57] ABSTRACT

AΔ¹ - tetrahydrophthalic anhydride is reacted with an amine in the presence of lower fatty acid. Alternatively N-(4-hydroxyphenyl)-Δ¹-tetrahydrophthalimide or a salt thereof is reacted with an aralkyl halide. A N-substituted-Δ¹-tetrahydrophthalimide compound having herbicidal activity is produced. This compound has the formula

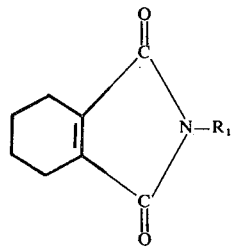

wherein R' is naphthyl; phenyl; phenyl substituted by 1–3 substituents selected from the group consisting of halogen, nitro, cyano, thiocyano, carboxyl, haloalkyl, lower alkyl and alkylthio; —CH₂Y wherein Y is phenyl, naphthyl or phenyl substituted by 1–5 substituents selected from the group consisting of halogen, nitro, lower alkyl and lower alkoxyl; or

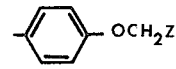

wherein Z is phenyl, naphthyl, or phenyl substituted by at least one substituent selected from the group consisting of halogen, nitro, lower alkyl and lower alkoxyl.

6 Claims, No Drawings

HERBICIDAL N-SUBSTITUTED-Δ¹-TETRAHYDROPHTHALIMIDE

The present application is a divisional application of Ser. No. 207,957, filed Dec. 14, 1971, now U.S. Pat. No. 3,878,224, and which claims the priority of Japanese application Nos. 45-115868, filed Dec. 23, 1970, 46-81083 filed Oct. 14, 1971, 46-82349 filed Oct. 18, 1971, and 46-84803 filed Oct. 26, 1971.

BACKGROUND OF THE INVENTION

This invention relates to herbicides particularly to herbicides that contain as active ingredient N-substituted-Δ¹-tetrahydrophthalimides. The invention also relates to said N-substituted Δ¹-tetrahydrophthalimides.

The method of manufacture and physical properties of some N-substituted-tetrahydrophthalimides are known in the art. For example, it has been reported in Berichte der Deutschen Chemischen Gesellschaft 1903 pp. 996–1007 that N-substituted-Δ¹-tetrahydrophthalimides were obtained by heating Δ¹-tetrahydrophthalic anhydride and primary amine in an alcoholic solution. Reference is made to physical properties such as crystal form, melting point and the like with regard to N-phenyl-Δ¹-tetrahydrophthalimide, N-(p-hydroxyphenyl)-Δ¹-tetrahydrophthalimide, N-(p-methoxyphenyl)-Δ¹-tetrahydrophthalimide and N-(p-ethoxyphenyl)-Δ¹-tetrahydrophthalimide. This report is referred to in Chemisches Zentralblatt 1906, II, pp. 876–877.

It should be understood that the disclosure in said prior publications is limited only to the method of manufacture and physical properties of specific N-substituted-Δ¹-tetrahydrophthalimides.

SUMMARY OF THE INVENTION

It is, therefore, an object of this invention to provide improved herbicides containing as active ingredient the N-substituted-Δ¹-tetrahydrophthalimide derivative.

Another object of this invention is to provide novel N-substituted-Δ¹-tetrahydrophthalimide derivatives, which exhibit excellent herbicidal effect.

DETAILED DESCRIPTION OF THE INVENTION

In accordance with the present invention there is provided a herbicide containing as active ingredient at least one N-substituted-Δ¹-tetrahydrophthalimide, which is represented by the general formula

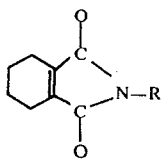

in which R denotes an aryl group or an aralkyl group. The benzene ring of the aryl or aralkyl group may contain one to five substituents selected from the group consisting of halogen, hydroxyl-, nitro-, cyano-, thiocyano-, carboxyl-, haloalkyl-, lower alkyl-, lower alkoxyl-, lower alkylthio-, phenyl and —O—CH₂A in which A denotes a phenyl, naphthyl, or phenyl substituted by at least one member selected from the group consisting of halogen, nitro, lower alkyl, and lower alkoxyl.

The phthalimide derivatives represented by the said general formula may be divided into three groups of compounds as follows:

1. Compounds represented by the formula

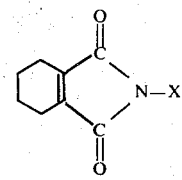 (I)

in which X is phenyl, naphthyl or phenyl substituted by at least one member selected from the group consisting of halogen, hydroxyl, nitro cyano, thiocyano, carboxyl, haloalkyl, lower alkyl, lower alkoxyl, lower alkylthio, and phenyl.

2. Compounds represented by the general formula

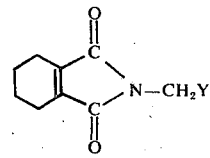 (II)

in which Y is phenyl, naphthyl, or phenyl substituted by at least one member selected from the group consisting of halogen, nitro, lower alkyl, and lower alkoxyl.

3. Compounds represented by the general formula

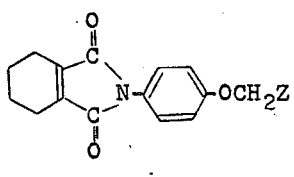 (III)

in which Z is phenyl, naphthyl, or phenyl substituted by at least one member selected from the group consisting of halogen, nitro, lower alkyl, and lower alkoxyl.

The imides represented by the formula (I) may be manufactured by the method disclosed in the aforesaid Berichte reference in which Δ¹-tetrahydrophthalic anhydride and aniline or a derivative thereof are heated in an alcoholic solution. However, such method is not practical from a commercial view point because it affords of a low yield of the product imides.

This problem is solved by the present invention in accordance with which the imides represented by the formula (I) are commercially produced in a higher yield by reacting Δ¹-tetrahydrophthalic anhydride with an aryl amine in the presence of lower fatty acids.

Examples of such lower fatty acids include acetic acid, propionic acid and butyric acid. Acetic acid is generally preferred. No limits are set with respect to the amount of lower fatty acid employed. Although it is effective even in a small amount, it usually is used in an amount equivalent to 0.1 to 20.0 times the weight of Δ¹-tetrahydrophthalic anhydride. The reaction is facilitated by heating at a temperature in the range 40°–200°C, preferably 50°–150°C. A reaction solvent inert to the reaction, such as for example, acetone, dioxane, methyl ethyl ketone, tetrahydrofuran, carbon tetrachloride, benzene, toluene, xylene etc., may be used. Acid catalyst or dehydrating agent may also be used.

The imides represented by the formula (II) are novel and have never been referred to in prior publications. The imides may be manufactured by a method analogous to that which is employed for manufacturing the compounds of the formula (I) which method comprises reacting Δ¹-tetrahydrophthalic anhydride with aralkyl amine as follows:

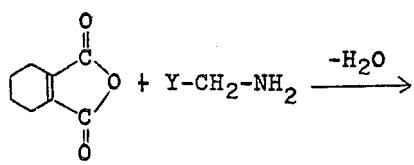

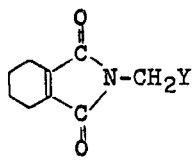

in which Y is as previously defined with regard to the formula (II).

The reaction takes place with or without solvent under heating for one to five hours. Preferred solvents include a lower fatty acid, for example, acetic acid or propionic acid, or an alcohol, for example, methanol or ethanol.

The imides represented by the formula (II) may also be manufactured by reacting Δ¹-tetrahydrophthalimide resulting from the reaction between Δ¹-tetrahydrophthalic anhydride and urea with aralkyl halide as follows:

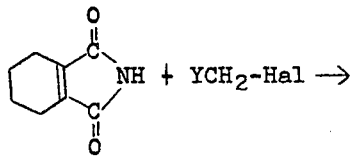

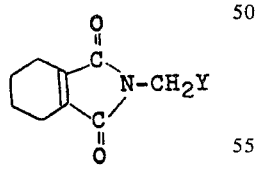

in which Y has the same meaning as in the formula (II) and Hal denotes halogen atom.

The reaction is carried out in a suitable solvent containing a basic substance, and conveniently at a temperature in the range of 50°–150°C. Examples of the solvents include benzene, toluene, acetone, methyl ethyl ketone, dioxane, tetrahydrofuran and carbon tetrachloride. Examples of suitable basic substances include inorganic or organic bases, for example, sodium bicarbonate, potassium carbonate, or pyridine, quinoline, dimethylaniline and triethylamine.

The imides represented by the formula (III) are also novel and have never been referred to in prior publications. These imides may be manufactured by reaction N-(4-hydroxyphenyl)-Δ¹-tetrahydrophthalimide resulting from the reaction between Δ¹-tetrahydrophthalic anhydride and 4-aminophenol or a salt of said tetrahydrophthalimide, for example, potassium-, sodium-, ammonium-, or amine salt, with an aralkyl halide as represented by the following formula:

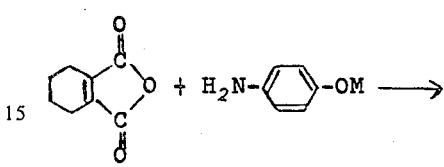

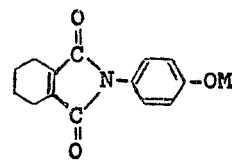

in which M is hydrogen, alkali metal, an ammonium group or an amine residue, Z is as defined with regard to the formula (III), and Hal denotes halogen atom.

The reaction takes place in a suitable solvent containing a basic compound, and advantageously under heating at a temperature in the range of 50°–150°C. As regards the solvent and basic compound, those referred to in the manufacturing method of the compounds of the formula (II) may be employed.

Examples of the method for manufacturing the compounds represented by the formulae (I), (II) and (III) are as follows:

REFERENCE EXAMPLE 1

15.2 g (0.1 mole) Δ¹-tetrahydrophthalic anhydride and 12.8 g (0.2 mole) 4-chloroaniline were refluxed for 30 minutes, under heating, in 50 ml of acetic acid. The reaction mixture was cooled. The light yellow flaky crystals which were produced were filtered off, washed with water and dried. 25.4 g of a compound having a melting point of 166°–167°C, and the following formula

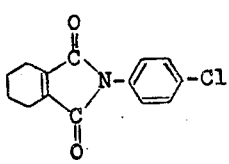

were obtained. This represented a yield of 97.1%.

An elemental analysis of the compound was as follows:

| | C,% | H,% | O,% | N,% |
|---|---|---|---|---|
| Calcd. for $C_{14}H_{12}O_2NCl$ | 64.25 | 4.62 | 12.23 | 5.35 |
| Analysis found | 64.22 | 4.75 | 12.39 | 5.41 |

REFERENCE EXAMPLE 2

15.2 g (0.1 mole) Δ¹-tetrahydrophthalic anhydride and 11.1 g 4-fluoroaniline were refluxed for 30 minutes under heating in 50 ml of propionic acid. The reaction mixture was cooled. The white capillary crystals which were produced were filtered off and dried. 23.2 g of a compound melting at 152°–154°C, and having the formula

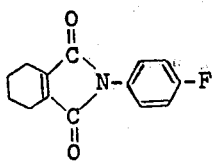

were obtained. This represented a yield of 94.7%.

An elemental analysis of the compound was as follows:

|  | C,% | H,% | O,% | N,% |
|---|---|---|---|---|
| Calcd. for C₁₄H₁₂O₂NF | 68.56 | 4.93 | 13.05 | 5.71 |
| Analysis found | 68.62 | 4.89 | 13.18 | 5.58 |

REFERENCE EXAMPLE 3

4.6 g of Δ¹-tetrahydrophthalic anhydride were dissolved in 15 g of acetic acid, and 3.2 g of benzylamine were added. After a 1 hour reflux under heating, a quantity of water was poured into the reaction mixture. The organic layer was extracted with benzene. The extract was dried with magnesium sulphate, purged of excess solvent and distilled under reduced pressure. 6 g of a compound having the formula

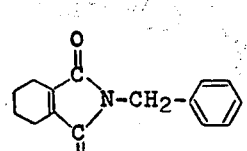

and boiling at 163°C/3 mm Hg were obtained. An elemental analysis of the compound was as follows:

|  | C,% | H,% | O,% | N,% |
|---|---|---|---|---|
| Calcd. for C₁₅H₁₅NO₂ | 74.66 | 6.27 | 13.26 | 5.81 |
| Analysis found | 74.48 | 6.25 | 13.19 | 5.60 |

REFERENCE EXAMPLE 4

4.6 g Δ¹-tetrahydrophthalic anhydride and 5.3 g 3,4-dichlorobenzylamine were refluxed for 5 hours under heating, in 30 g of ethanol. A suitable amount of water was poured into the reaction mixture. The resulting crystals were filtered off, washed with water once or twice and recrystallized from ethanol. 7.5 g of a compound having the formula

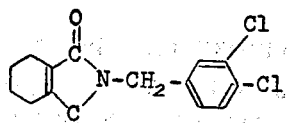

and melting at 90°C were obtained. An elemental analysis of the compound was as follows:

|  | C,% | H,% | O,% | N,% |
|---|---|---|---|---|
| Calcd. for C₁₅H₁₃NO₂Cl₂ | 58.08 | 4.22 | 10.32 | 4.52 |
| Analysis found | 57.87 | 4.29 | 10.40 | 4.72 |

REFERENCE EXAMPLE 5

The same method as in Reference Example 3 was followed to obtain from 4.6 g Δ¹-tetrahydrophthalic anhydride and 3.6 g 4-methylbenzylamine 5.8 g of a compound having the formula

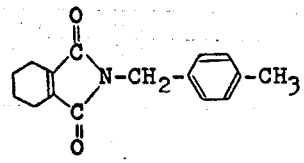

and a boiling point of 159°–160°C/3 mm Hg.

An elemental analysis of the compound was as follows:

|  | C,% | H,% | O,% | N,% |
|---|---|---|---|---|
| Calcd. for C₁₆H₁₇NO₂ | 75.27 | 6.71 | 12.53 | 5.48 |
| Analysis found | 74.99 | 6.55 | 12.39 | 5.41 |

REFERENCE EXAMPLE 6

Reference example 4 was repeated with 4.6 g Δ¹-tetrahydrophthalic anhydride and 4.1 g 4-methoxybenzylamine to obtain 6.4 g of a compound having the formula

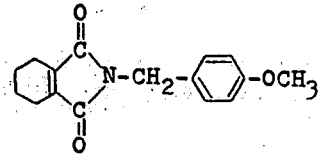

and a boiling point of 180°–185°C/4 mm Hg.

An elemental analysis of the compound was as follows:

|  | C,% | H,% | O,% | N,% |
|---|---|---|---|---|
| Calcd. for C₁₆H₁₇NO₃ | 70.82 | 6.32 | 17.69 | 5.16 |
| Analysis found | 70.77 | 6.30 | 17.54 | 5.0 |

REFERENCE EXAMPLE 7

4.5 g Δ¹-tetrahydrophthalimide, 5.1 g benzylbromide and 5.4 anhydrous potassium carbonate were refluxed for 8 hours, with stirring and heating, in 100 g of methyl ethyl ketone. The reaction mixture was filtered while hot. The filtrate was concentrated and distilled under reduced pressure. 6.5 g of a compound having the formula

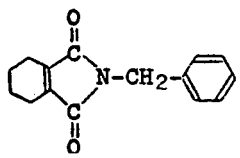

and a boiling point of 163°C/3 mm Hg were obtained. An elemental analysis of the compound was as follows:

|  | C,% | H,% | O,% | N,% |
|---|---|---|---|---|
| Calcd. for C₁₅H₁₅NO₂ | 74.66 | 6.27 | 13.26 | 5.81 |
| Analysis found | 74.39 | 6.03 | 13.42 | 5.47 |

REFERENCE EXAMPLE 8

4.5 g Δ¹-tetrahydrophthalimide, 4.8 g 3-chlorobenzyl chloride and 3.6 g pyridine were refluxed for 8 hours, under heating, in 100 g of toluene. The reaction mixture was filtered while hot, and the filtrate was concentrated. A Suitable amount of water was added to the residue for extraction with benzene. The extract was dried with magnesium sulphate, purged of excess solvent, and distilled under reduced pressure. 6.7 g of a compound having the formula

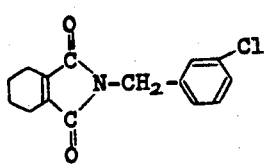

and a boiling point of 170°C/3 mm Hg were obtained. An elemental analysis of the compound was as follows:

|  | C,% | H,% | O,% | N,% |
|---|---|---|---|---|
| Calcd. for C₁₅H₁₄NO₂Cl | 65.34 | 5.12 | 11.61 | 5.08 |
| Analysis found | 65.09 | 5.19 | 11.57 | 5.11 |

REFERENCE EXAMPLE 9

4.5 g Δ¹-tetrahydrophthalimide, 4.7 g 2,4-dimethylbenzyl chloride and 4.5 g triethylamine were refluxed for 8 hours, under heating, in 100 g of dioxane. The reaction mixture was filtered, and the filtrate was concentrated. A suitable amount of water was added to the residue. The resulting crystals was filtered off and recrystallized from ethanol. 5.2 g of a compound having the formula

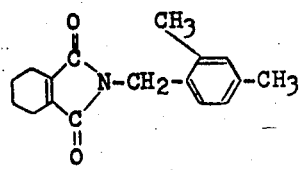

and a melting point of 74°C were obtained. An elemental analysis of the compound was as follows:

|  | C,% | H,% | O,% | N,% |
|---|---|---|---|---|
| Calcd. for C₁₇H₁₉NO₂ | 75.80 | 7.11 | 11.88 | 5.20 |
| Analysis found | 75.61 | 7.39 | 11.77 | 5.19 |

REFERENCE EXAMPLE 10

4.9 g N-(4-hydroxyphenyl)-Δ¹-tetrahydrophthalimide, 3.4 g benzylbromide and 3 g anhydrous potassium carbonate were refluxed for 5 hours in 100 g of acetone. The reaction mixture was filtered, and the filtrate was concentrated. The resulting crystals were recrystallized from benzene. 5.9 g of a compound having the formula

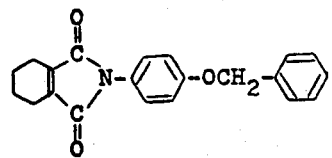

and a melting point of 188°–189°C were obtained. An elemental analysis of the compound was as follows:

|  | C,% | H,% | O,% | N,% |
|---|---|---|---|---|
| Calcd. for C₂₁H₁₉NO₃ | 75.66 | 5.74 | 14.40 | 4.20 |
| Analysis found | 75.82 | 5.87 | 14.50 | 4.24 |

REFERENCE EXAMPLE 11

4.9 g N-(4-hydroxyphyenyl)-Δ¹-tetrahydrophthalimide, 3.9 g 2,4-dichlorobenzyl chloride and 2.5 g pyridine were refluxed for 8 hours in 100 g of methyl ethyl ketone. The reaction mixture was filtered, and the filtrate was concentrated. The resulting crystals were recrystallized from benzene. 6.3 g of a compound having the formula

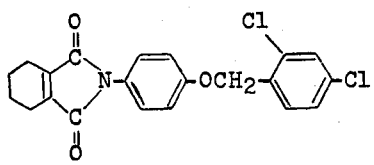

and a melting point of 143°–144°C were obtained. An elemental analysis of the compound was as follows:

|  | C,% | H,% | O,% | N,% |
|---|---|---|---|---|
| Calcd. for $C_{21}H_{17}NO_3Cl_2$ | 62.70 | 4.26 | 11.93 | 3.48 |
| Analysis found | 62.56 | 4.23 | 12.04 | 3.40 |

REFERENCE EXAMPLE 12

4.9 g N-(4-hydroxyphenyl)-$\Delta^1$-tetrahydrophthalimide, 3.1 g 4-ethylbenzyl chloride and 3 g anhydrous potassium carbonate were refluxed for 10 hours in 100 g of toluene. The reaction mixture was filtered while hot, and excess solvent was distilled off. The resulting crystals were recrystallized from ethanol. 6.6 g of a compound having the formula

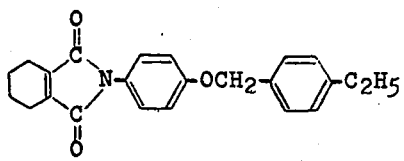

and a melting point of 134°–135°C were obtained. An elemental analysis of the compound was as follows:

|  | C,% | H,% | O,% | N,% |
|---|---|---|---|---|
| Calcd. for $C_{23}H_{23}NO_3$ | 76.43 | 6.41 | 13.28 | 3.88 |
| Analysis found | 76.14 | 6.41 | 13.25 | 3.84 |

REFERENCE EXAMPLE 13

4.9 g N-(4-hydroxyphenyl)-$\Delta^1$-tetrahydrophthalimide, 3.4 g 4-nitrobenzyl chloride and 3.3 g triethylamine were refluxed for 5 hours in 100 g of dioxane. The reaction mixture was filtered while hot, and excess solvent was distilled off. The resulting crystals were recrystallized from acetone. 6.8 g of a compound having the formula

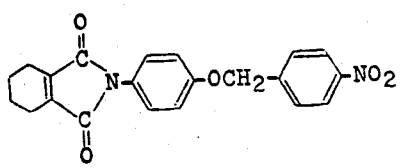

and a melting point of 188°–189°C were obtained. An elemental analysis of the compound was as follows:

|  | C,% | H,% | O,% | N,% |
|---|---|---|---|---|
| Calcd. for $C_{21}H_{13}N_2O_5$ | 66.66 | 4.79 | 21.14 | 7.41 |
| Analysis found | 66.54 | 4.91 | 21.23 | 7.19 |

REFERENCE EXAMPLE 14

5.3 g sodium salt of N-(4-hydroxyphenyl)-$\Delta^1$-tetrahydrophthalimide and 3.2 g 4-methylbenzyl chloride were refluxed for 5 hours in 100 g of methyl ethyl ketone. Insoluble matter was filtered off, and the filtrate was concentrated. The resulting crystals were recrystallized from benzene. 6.0 g of a product having the formula

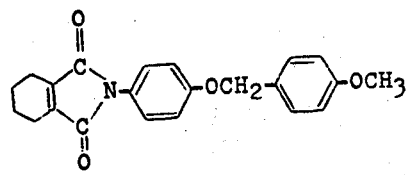

and a melting point of 171°–172.5°C were obtained. An elemental analysis of the compound was as follows:

|  | C,% | H,% | O,% | N,% |
|---|---|---|---|---|
| Calcd. for $C_{22}H_{21}O_4N$ | 72.71 | 5.82 | 17.61 | 3.85 |
| Analysis found | 72.61 | 5.91 | 17.77 | 3.97 |

Indicated in the following tables are compounds according to the invention which have been manufactured by the methods disclosed and have been found to be useful as an active ingredient of herbicides.

Table I-1

| No. | X | Melting point, °C | Elemental analysis *1 | | | |
|---|---|---|---|---|---|---|
|  |  |  | C,% | H,% | O,% | N,% |
| 1 | phenyl | 139–140 | 73.99 | 5.77 | 14.08 | 6.16 |
|  |  |  | 74.10 | 5.85 | 14.21 | 6.28 |
| 2 | 2-F-phenyl | 112.5–113 | 68.56 | 4.93 | 13.05 | 5.71 |
|  |  |  | 68.49 | 4.87 | 13.12 | 5.90 |
| 3 | 4-F-phenyl | 152–154 | 68.56 | 4.93 | 13.05 | 5.71 |
|  |  |  | 68.62 | 4.89 | 13.18 | 5.58 |

Table I-1-continued
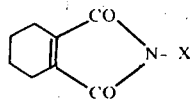
| No. | X | Melting point, °C | Elemental analysis *1 | | | |
|---|---|---|---|---|---|---|
| | | | C,% | H,% | O,% | N,% |
| 4 | 3-Cl-C6H4 | 86 | 64.25 / 64.31 | 4.62 / 4.51 | 12.23 / 12.13 | 5.35 / 5.40 |
| 5 | 4-Cl-C6H4 | 166–168 | 64.25 / 64.22 | 4.62 / 4.75 | 12.23 / 12.39 | 5.35 / 5.41 |
| 6 | 4-Br-C6H4 | 172–174 | 54.92 / 54.88 | 3.95 / 4.02 | 10.45 / 10.53 | 4.58 / 4.72 |
| 7 | 4-I-C6H4 | 161–162 | 47.61 / 47.84 | 3.42 / 3.44 | 9.06 / 9.02 | 3.97 / 3.87 |
| 8 | 3-CF3-C6H4 | 120–121 | 61.02 / 61.13 | 4.10 / 4.24 | 10.84 / 10.77 | 4.75 / 4.69 |
| 9 | 2,4-Cl2-C6H3 | 97–98 | 56.78 / 56.89 | 3.74 / 3.86 | 10.81 / 10.97 | 4.73 / 4.92 |
| 10 | 3,4-Cl2-C6H3 | 174 | 56.78 / 56.68 | 3.74 / 3.71 | 10.81 / 10.94 | 4.73 / 4.68 |
| 11 | 3-Cl-4-Br-C6H3 | 182–184 | 49.37 / 49.27 | 3.26 / 3.23 | 9.40 / 9.54 | 4.11 / 4.17 |
| 12 | 2,3,4-Cl3-C6H2 | 114–115 | 50.86 / 50.99 | 3.05 / 3.17 | 9.68 / 9.81 | 4.24 / 4.33 |
| 13 | 2-CH3-4-Cl-C6H3 | 152–153 | 65.34 / 65.18 | 5.12 / 5.00 | 11.61 / 11.77 | 5.08 / 5.07 |
| 14 | 2-CH3-4-Br-C6H3 | 169–170 | 56.27 / 56.39 | 4.41 / 4.28 | 9.99 / 10.11 | 4.38 / 4.52 |
| 15 | 2-OCH3-4-Cl-C6H3 | 129–130 | 61.76 / 61.79 | 4.84 / 4.81 | 16.45 / 16.66 | 4.80 / 4.70 |
| 16 | 2-OCH3-4-Br-C6H3 | 143–144 | 53.59 / 53.74 | 4.20 / 4.07 | 14.28 / 14.44 | 4.17 / 4.23 |
| 17 | 2-CH3-C6H4 | 136–137 | 74.66 / 74.73 | 6.27 / 6.25 | 13.26 / 13.18 | 5.81 / 5.71 |
| 18 | 4-CH3-C6H4 | 124–125 | 74.66 / 74.57 | 6.27 / 6.39 | 13.26 / 13.38 | 5.81 / 5.69 |

Table I-1-continued

| No. | X | Melting point, °C | Elemental analysis *1 C,% | H,% | O,% | N,% |
|---|---|---|---|---|---|---|
| 19 | -C₆H₄-C₂H₅ (para) | 122.5–123 | 75.27 / 75.34 | 6.71 / 6.85 | 12.53 / 12.71 | 5.49 / 5.62 |
| 20 | 2,6-dimethylphenyl | 168–169 | 75.27 / 75.25 | 6.71 / 6.78 | 12.53 / 12.48 | 5.49 / 5.41 |
| 21 | 2,3-dimethylphenyl | 153–154 | 75.27 / 75.09 | 6.71 / 6.70 | 12.53 / 12.67 | 5.49 / 5.58 |
| 22 | 2,6-diethylphenyl | 107–109 | 76.29 / 76.43 | 7.47 / 7.56 | 11.29 / 11.42 | 4.94 / 5.05 |
| 23 | 2-methoxyphenyl | 151–152 | 70.02 / 70.08 | 5.88 / 5.81 | 18.66 / 18.51 | 5.44 / 5.36 |
| 24 | 4-OCH₃-phenyl | 100 | 70.02 / 70.17 | 5.88 / 5.77 | 18.66 / 18.52 | 5.44 / 5.27 |
| 25 | 4-OC₂H₅-phenyl | 135 | 70.83 / 70.97 | 6.32 / 6.41 | 17.69 / 17.49 | 5.16 / 5.01 |
| 26 | 2-biphenyl | 118–120 | 79.18 / 79.23 | 5.65 / 5.72 | 10.55 / 10.49 | 4.62 / 4.52 |
| 27 | 4-biphenyl | 189–190 | 79.18 / 79.15 | 5.65 / 5.72 | 10.55 / 10.73 | 4.62 / 4.55 |
| 28 | 2-hydroxyphenyl | 206–208 | 69.12 / 69.09 | 5.39 / 5.31 | 19.73 / 19.84 | 5.76 / 5.91 |
| 29 | 4-NO₂-phenyl | 175–177 | 61.76 / 61.58 | 4.44 / 4.35 | 23.51 / 23.72 | 10.29 / 10.35 |
| 30 | 4-SCH₃-phenyl | 104–105 | 65.91 / 65.85 | 5.53 / 5.41 | 11.71 / 11.83 | 5.12 / 5.05 |
| 31 | 4-COOH-phenyl | 254–256 | 66.41 / 66.62 | 4.83 / 4.97 | 23.59 / 23.72 | 5.16 / 5.08 |
| 32 | 2,5-dichloro-4-SCN-phenyl | 155 | 51.01 / 51.00 | 2.85 / 2.97 | 9.06 / 9.16 | 7.93 / 7.99 |

Table I-1-continued

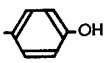

| No. | X | Melting point, °C | Elemental analysis *1 | | | |
|---|---|---|---|---|---|---|
| | | | C,% | H,% | O,% | N,% |
| 33 | 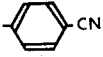—OH | 183–184 | 69.12<br>69.01 | 5.39<br>5.17 | 19.73<br>19.58 | 5.76<br>5.57 |
| 34 | 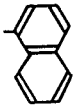—CN | 144–145 | 71.41<br>71.58 | 4.80<br>4.91 | 12.69<br>12.74 | 11.11<br>10.97 |
| 35 |  | 163–164 | 77.96<br>78.00 | 5.45<br>5.57 | 11.54<br>11.71 | 5.05<br>5.14 |

Note *1
Figures in the upper rows represent theoretical values which have been calculated for the formulae. Figures in the lower rows represent actual values found by elemental analyses of the compounds numbered 1 to 35.

Table I-2

| No. | Y | Properties | Elemental analysis *1 | | | |
|---|---|---|---|---|---|---|
| | | | C,% | H,% | O,% | N,% |
| 36 |  | b.p.<br>163°C/3 mm Hg | 74.66<br>74.48<br>74.39 | 6.27<br>6.25<br>6.03 | 13.26<br>13.19<br>13.42 | 5.81<br>5.60<br>5.47 |
| 37 |  (Cl ortho) | m.p.<br>111–112°C | 65.34<br>65.21<br>65.19 | 5.12<br>5.30<br>5.00 | 11.61<br>11.78<br>11.73 | 5.08<br>5.21<br>5.04 |
| 38 |  (Cl meta) | b.p.<br>170°C/3 mm Hg | 65.34<br>65.47<br>65.09 | 5.12<br>5.02<br>5.19 | 11.61<br>11.81<br>11.57 | 5.08<br>5.00<br>5.11 |
| 39 | —Cl | m.p.<br>43–44°C | 65.34<br>65.46<br>65.42 | 5.12<br>5.05<br>5.07 | 11.61<br>11.74<br>11.66 | 5.08<br>5.11<br>5.07 |
| 40 | —Br | $n_D^{20}$: 1.5858 | 56.27<br>56.32<br>56.18 | 4.41<br>4.29<br>4.58 | 9.99<br>10.07<br>10.01 | 4.38<br>4.51<br>4.26 |
| 41 | —F | $n_D^{20}$: 1.5515 | 69.49<br>69.62<br>69.63 | 5.44<br>5.28<br>5.52 | 12.34<br>12.46<br>12.51 | 5.40<br>5.27<br>4.54 |
| 42 | 2,6-Cl<sub>2</sub>-phenyl | m.p.<br>124–125°C | 58.08<br>58.13<br>58.12 | 4.22<br>4.07<br>4.08 | 10.32<br>10.44<br>10.43 | 4.52<br>4.73<br>4.62 |
| 43 | 2,3-Cl<sub>2</sub>-phenyl | m.p.<br>90°C | 58.08<br>57.87<br>57.99 | 4.22<br>4.29<br>4.17 | 10.32<br>10.40<br>10.18 | 4.52<br>4.42<br>4.39 |
| 44 | 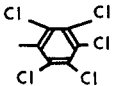 (pentachlorophenyl) | m.p.<br>164–165°C | 43.57<br>43.49<br>43.62 | 2.44<br>2.29<br>2.26 | 7.74<br>7.91<br>7.82 | 3.39<br>3.52<br>3.46 |

Table I-2-continued $$\text{structure: cyclohexene-fused } \begin{array}{c}CO\\CO\end{array}\!\!\!>\!\!N\text{—}CH_2Y$$

| No. | Y | Properties | Elemental analysis *1 | | | |
|---|---|---|---|---|---|---|
| | | | C,% | H,% | O,% | N,% |
| 45 | –C₆H₄–CH₃ | b.p. 159–160°C/3 mm Hg | 75.27<br>74.99<br>75.33 | 6.71<br>6.55<br>6.63 | 12.53<br>12.39<br>12.47 | 5.48<br>5.41<br>5.54 |
| 46 | 2,4-(H₃C)(CH₃)C₆H₃– | m.p. 74°C | 75.81<br>75.83<br>75.61 | 7.11<br>7.28<br>7.39 | 11.88<br>12.00<br>11.77 | 5.20<br>5.09*<br>5.19 |
| 47 | 2-CH₃, 5-CH₃ dimethylphenyl | m.p. 73–74°C | 75.81<br>75.99<br>75.77 | 7.11<br>7.22<br>7.07 | 11.88<br>11.97<br>11.97 | 5.20<br>5.24<br>5.32 |
| 48 | –C₆H₄–OCH₃ | b.p. 180–185°C/4 mm Hg | 70.82<br>70.77<br>71.02 | 6.32<br>6.30<br>6.16 | 17.69<br>17.54<br>17.74 | 5.16<br>5.01<br>5.10 |
| 49 | –C₆H₄–NO₂ | m.p. 118–120°C | 62.93<br>63.02<br>62.80 | 4.93<br>5.07<br>4.97 | 22.36<br>22.23<br>22.40 | 9.79<br>9.81<br>9.90 |
| 50 | naphthyl | $n_D^{20}$: 1.6620 | 78.33<br>78.29<br>78.40 | 5.88<br>5.78<br>5.84 | 10.98<br>10.79<br>11.07 | 4.81<br>4.80<br>4.86 |
| 51 | –C₆H₄–i-C₃H₇ | $n_D^{20}$: 1.5427 | 76.29<br>76.37<br>76.16 | 7.47<br>7.51<br>7.39 | 11.29<br>11.41<br>11.42 | 4.94<br>5.03<br>5.02 |

Note *1
Figures in the top rows represent theoretical values calculated for the formulae; the figures in the middle rows were determined by elemental analyses (Δ¹-tetrahydrophthalic anhydride being used as the starting material); and the figures in the bottom rows were determined by elemental analyses (Δ¹-tetrahydrophthalimide being employed as the starting material).

Table I-3

$$\text{structure: cyclohexene-fused } \begin{array}{c}CO\\CO\end{array}\!\!\!>\!\!N\text{—}C_6H_4\text{—}OCH_2Z$$

| No. | Z | Melting point, °C | Elemental analysis *1 | | | |
|---|---|---|---|---|---|---|
| | | | C,% | H,% | O,% | N,% |
| 52 | –C₆H₅ | 188–189 | 75.66<br>75.72 | 5.74<br>5.87 | 14.40<br>14.50 | 4.20<br>4.24 |
| 53 | 2-Cl-C₆H₄– | 152 | 68.57<br>68.49 | 4.93<br>5.01 | 13.05<br>13.11 | 3.81<br>3.94 |
| 54 | –C₆H₄–Cl | 162–164 | 68.57<br>68.48 | 4.93<br>4.90 | 13.05<br>13.21 | 3.81<br>3.67 |
| 55 | –C₆H₄–Br | 180 | 61.18<br>61.29 | 4.40<br>4.44 | 11.64<br>11.72 | 3.40<br>3.57 |
| 56 | –C₆H₄–F | 159 | 71.78<br>71.92 | 5.16<br>5.27 | 13.66<br>13.79 | 3.99<br>4.00 |

Table I-3-continued

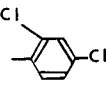

| No. | Z | Melting point, °C | Elemental analysis *1 | | | |
|---|---|---|---|---|---|---|
| | | | C,% | H,% | O,% | N,% |
| 57 | 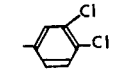 | 143–144 | 62.70<br>62.56 | 4.26<br>4.23 | 11.93<br>12.04 | 3.48<br>3.40 |
| 58 | 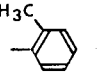 | 157–158 | 62.70<br>62.72 | 4.26<br>4.29 | 11.93<br>12.03 | 3.48<br>3.57 |
| 59 | 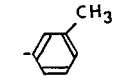 | 172–174 | 76.06<br>76.17 | 6.09<br>6.01 | 13.82<br>13.77 | 4.03<br>4.16 |
| 60 | 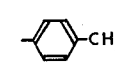 | 170–171 | 76.06<br>76.00 | 6.09<br>6.12 | 13.82<br>13.77 | 4.03<br>4.14 |
| 61 | 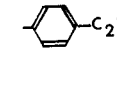-CH$_3$ | 181 | 76.06<br>76.11 | 6.09<br>6.02 | 13.82<br>14.00 | 4.03<br>4.11 |
| 62 | 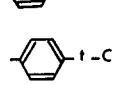-C$_2$H$_5$ | 134–135 | 76.43<br>76.14 | 6.41<br>6.41 | 13.28<br>13.25 | 3.88<br>3.84 |
| 63 | 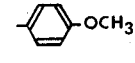-i-C$_3$H$_7$ | 160–161 | 76.77<br>76.88 | 6.71<br>6.49 | 12.78<br>12.88 | 3.73<br>3.58 |
| 64 | -t-C$_4$H$_9$ | 170–171 | 77.09<br>77.12 | 6.99<br>6.87 | 12.32<br>12.41 | 3.60<br>3.81 |
| 65 | 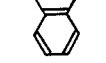-OCH$_3$ | 171–172.5 | 72.71<br>72.61 | 5.82<br>5.91 | 17.61<br>17.77 | 3.85<br>3.97 |
| 66 | -NO$_2$ | 188–189 | 66.66<br>66.54 | 4.79<br>4.91 | 21.14<br>21.23 | 7.41<br>7.19 |
| 67 | 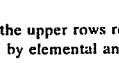 | 186–187 | 78.31<br>78.51 | 5.52<br>5.63 | 12.52<br>12.47 | 3.65<br>3.74 |

Note *1
Figures given in the upper rows represent theoretical values calculated for the formulae and those in the lower rows were determined by elemental analyses.

The imides indicated in the above tables may be employed for herbicidal purposes as is. They are, however, normally used in the form of a dilution in an inert liquid or solid. If desired a surfactant or the like may be added to the imides for use in the form of dust, wettable powder, emulsion or granules. Other substances may be incorporated with the imides, such as for example fertilizers, fungicides, insecticides, nematocides, synergistic herbicides, or other types of herbicides and plant growth regulants.

A great variety of liquids may be employed as carriers for the herbicides of the instant invention. Examples of such liquids include organic liquids such as hydrocarbons, for example, kerosene, benzene and xylene; halogenated hydrocarbons, for example, chlorobenzene and dichloroethylene; alcohols and acetone. Examples of solid carriers include bentonite, kaolin, clay, talc, Japanese acid clay, diatomaceous earth, silica sand and calcium carbonate.

Examples of suitable surfactants include alkylbenzene sulphonate, lignin sulphonate, higher alcohol sulphates, polyoxyethylene fatty acid esters, polyoxyethylene sorbitan fatty acid esters, dialkylsulphosuccinate and alkyltrimethylammonium chloride.

Examples of formulations containing the herbicides of the present invention are as follows:

"Dust"

5 parts by weight of the compound No. 3 of Table I were thoroughly mixed with 95 parts by weight of clay to give a dust containing 5% of active ingredient.

"Wettable Powder"

50 parts by weight of the compound No. 62 of Table I were thoroughly mixed with 45 parts by weight of diatomaceous earth and 5 parts by weight of "Solpole 8070" (tradename of a surfactant manufactured by Toho Chemical Industries Limited, of Japan) to obtain a wettable powder containing 50% of active ingredient, which was diluted with water to a desired concentration for spraying.

"Emulsion"

30 parts by weight of compound No. 39 of Table I were dissolved in a mixture of 35 parts by weight of toluene and 30 parts by weight of ethanol, and 5 parts by weight of "Solpole 800 A" (tradename of a surfactant manufactured by Toho Chemical Industries Limited, of Japan) were added thereto to form a solution containing 30% of active ingredient. The solution was diluted with water to produce an emulsion having a desired concentration for use as a spray.

"Granules"

A mixture of 6 parts by weight of the compound No. 27 of Table I, 25 parts by weight of bentonite, 50 parts by weight of talc, 16 parts by weight of white carbon and 3 parts by weight of "Solpole 9266" (tradename of a surfactant manufactured by Toho Chemical Industries Ltd., of Japan) was thoroughly kneaded together with water in an amount corresponding to 18% of the mixture by means of a kneading machine and granulated by means of a granulator provided with a 8 mm-mesh screen. The granules were dried at 60°C for 2 hours to give a final product containing 6% of active ingredient. This product was scattered over weeds by means of a suitable device.

Although the herbicides of the present invention may be used for foliar treatment, they are particularly suitable for soil treatment.

The amount of herbicides used is preferably but not in a limitative sense in the range of 3–50 g per are. The herbicides of the present invention are activated by sunshine to give better herbicidal effect. This is illustrated in the following examples 10 and 11 in which in the presence of sunshine it was determined that the amount of herbicide used could be reduced to 3 to 20 g per are to produce adequate herbicidal effect.

The invention will now be illustrated with reference to some embodiments in which the numbers of the compounds correspond to those in Tables I-1, I-2 and I-3. It should be noted that examples 1 to 9 were carried out in a green house whereas examples 10 and 11 were carried out outdoors.

EXAMPLE 1

A Wagner pot of 1/2000 are was filled with "paddy" soil, and an amount of water was added to the soil and kneaded thoroughly. Evenly spread over the surface of the pot was a prescribed amount of paddy soil in which undesirable weeds such as toothcup (Rotala indica Koehne) and millet (Echinochloa Crus-galli) were apt to grow. Three-leafed paddy rice seedlings were transplanted in the pot and kept in the paddy field state for 7 days. An aqueous suspension of the wettable powder of the compounds indicated in the following table was sprayed over the water surface of the pot. 25 days later, the growth of the said grasses was compared with the non-treated plot. The results are shown in the following Table 2 in which the herbicidal effect (sprouting-inhibiting effect) on the grasses was evaluated and expressed by the figures 0 to 5 according to the following scale:

Table 2

| Compound No. | Appln rate, g/are | Herbicidal effect | | |
|---|---|---|---|---|
| | | Rice seedling | Toothcup | Millet |
| 1 | 40 | 0 | 2 | 3 |
| | 20 | 0 | 1 | 1 |
| 3 | 40 | 0 | 5 | 5 |
| | 20 | 0 | 5 | 5 |
| 4 | 40 | 0 | 5 | 5 |
| | 20 | 0 | 5 | 5 |
| 8 | 40 | 0 | 5 | 5 |
| | 20 | 0 | 4 | 5 |
| 10 | 40 | 0 | 5 | 5 |
| | 20 | 0 | 5 | 5 |
| 11 | 40 | 0 | 4 | 5 |
| | 20 | 0 | 2 | 4 |
| 13 | 40 | 0 | 3 | 4 |
| | 20 | 0 | 2 | 3 |
| 15 | 40 | 1 | 5 | 5 |
| | 20 | 0 | 4 | 5 |
| 17 | 40 | 0 | 3 | 3 |
| | 20 | 0 | 1 | 2 |
| 18 | 40 | 0 | 2 | 3 |
| | 20 | 0 | 2 | 2 |
| 20 | 40 | 0 | 5 | 5 |
| | 20 | 0 | 5 | 5 |
| 21 | 40 | 0 | 4 | 5 |
| | 20 | 0 | 3 | 3 |
| 24 | 40 | 0 | 4 | 4 |
| | 20 | 0 | 3 | 4 |
| 27 | 40 | 0 | 5 | 5 |
| | 20 | 0 | 4 | 5 |
| 28 | 40 | 1 | 3 | 4 |
| | 20 | 0 | 2 | 3 |
| 30 | 40 | 1 | 4 | 5 |
| | 20 | 0 | 2 | 3 |
| 31 | 40 | 1 | 4 | 3 |
| | 20 | 0 | 3 | 2 |
| 33 | 40 | 0 | 3 | 3 |
| | 20 | 0 | 2 | 2 |
| 34 | 40 | 0 | 5 | 5 |
| | 20 | 0 | 4 | 5 |
| 35 | 40 | 1 | 5 | 5 |
| | 20 | 0 | 3 | 4 |
| Non-treated plot | — | 0 | 0 | 0 |

| Figure | Herbicidal effect, % |
|---|---|
| 0 | 0 – 10 |
| 1 | 11 – 30 |
| 2 | 31 – 50 |
| 3 | 51 – 70 |
| 4 | 71 – 90 |
| 5 | 91 – 100 |

Note:
The figure 0, for example, means that the grasses were killed 0 to 10 per cent in relation to the non-treated plot.

EXAMPLE 2

A Wagner pot of 1/2000 are was filled with paddy soil, and an amount of water was added. After thorough kneading, a prescribed amount of paddy soil in which slender spickrush (Eleocharis acicularis) was apt to grow was spread over the surface of the pot, and paddy rice seedlings in the three-leafed stage were transplanted in the pot and kept in the paddy field state for 7 days. An aqueous suspension of the wettable powder of the compounds, i.e. imides indicated in the following table was sprayed over the water surface of the pot. 25 days after this treatment, the growth of the plant was investigated. The results are shown in the following table in which the herbicidal effect was evaluated in a manner analogous to example 1.

Table 3

| Compound No. | Appln rate, g/are | Herbicidal effect | |
|---|---|---|---|
| | | Rice seedling | Slender spickrush |
| 3 | 40 | 0 | 3 |
| | 20 | 0 | 2 |
| 4 | 40 | 0 | 3 |
| | 20 | 0 | 1 |
| 8 | 40 | 0 | 3 |
| | 20 | 0 | 2 |
| 15 | 40 | 0 | 3 |
| | 20 | 0 | 2 |
| 20 | 40 | 0 | 3 |
| | 20 | 0 | 3 |
| 21 | 40 | 0 | 3 |
| | 20 | 0 | 1 |
| 27 | 40 | 0 | 3 |
| | 20 | 0 | 2 |
| Non-treated plot | — | 0 | 0 |

EXAMPLE 3

A pot of one two-thousandth are was seeded with radish and millet. When the radish began to sprout the true leaf and the millet was in the two-leafed period, the compounds indicated in the following table were formulated as an aqueous suspension of wettable powder and sprayed on the terrestrial parts of the grasses in the pot. 20 days after the treatment, the growth of the grasses was investigated. The following Table 4 shows is the herbicidal effect of the test compounds which effect was evaluated in terms of figures 0 to 5 according to the following scale:

Table 4

| Compound No. | Appln rate, g/are | Herbicidal effect | |
|---|---|---|---|
| | | Radish | Millet |
| 2 | 40 | 5 | 5 |
| | 20 | 3 | 5 |
| 3 | 40 | 5 | 5 |
| | 20 | 5 | 5 |
| 5 | 40 | 4 | 4 |
| | 20 | 2 | 3 |
| 6 | 40 | 4 | 4 |
| | 20 | 2 | 3 |
| 7 | 40 | 4 | 3 |
| | 20 | 2 | 2 |
| 9 | 40 | 5 | 4 |
| | 20 | 3 | 3 |
| 12 | 40 | 5 | 5 |
| | 20 | 5 | 5 |
| 13 | 40 | 5 | 4 |
| | 20 | 4 | 3 |
| 14 | 40 | 5 | 5 |
| | 20 | 4 | 4 |
| 16 | 40 | 4 | 3 |
| | 20 | 3 | 1 |
| 19 | 40 | 3 | 4 |
| | 20 | 2 | 2 |
| 22 | 40 | 4 | 5 |
| | 20 | 3 | 5 |
| 23 | 40 | 4 | 4 |
| | 20 | 3 | 2 |
| 25 | 40 | 5 | 4 |
| | 20 | 3 | 3 |
| 26 | 40 | 5 | 4 |
| | 20 | 4 | 3 |
| 29 | 40 | 5 | 5 |
| | 20 | 5 | 3 |
| 32 | 40 | 5 | 4 |
| | 20 | 3 | 1 |
| Non-treated plot | — | 0 | 0 |

Table 4-continued

| Figure | Herbicidal effect |
|---|---|
| 0 | none |
| 1 | poor |
| 2 | slight |
| 3 | fair |
| 4 | good |
| 5 | excellent |

EXAMPLE 4

A Wagner pot of 1/5000 are was filled with farm soil and seeded with rice, soya bean and Indian corn 2 to 3 cm deep. Seeds of crabgrass (Digitoria ads cendens Henr) were sowed in the upper layer of the soil. The compounds of the following table were formulated as an aqueous suspension of wettable powder and sprayed on the soil layer. The rate of spray applied was such that an application rate of 10 g and 20 g of active ingredient per are was evaluated. 25 days later, the fresh weight of survival crabgrass was determined and compared with that of the non-treated plot in per cent. Concurrently, the phytotoxicity on rice, soya bean and Indian corn was also investigated. The results are shown in the following table in which the assigned figures 0 to 5 are as defined in Example 1.

Table 5

| Compounds No. | Appln rate, g/are | Phytotoxicity | | | Relative *1 amount of crabgrass alive, % |
|---|---|---|---|---|---|
| | | Rice | Soya bean | Indian corn | |
| 36 | 10 | 0 | 0 | 0 | 63 |
| | 20 | 0 | 0 | 0 | 48 |
| 37 | 10 | 0 | 0 | 0 | 43 |
| | 20 | 0 | 0 | 1 | 27 |
| 39 | 10 | 0 | 0 | 0 | 35 |
| | 20 | 0 | 0 | 1 | 19 |
| 42 | 10 | 0 | 0 | 0 | 38 |
| | 20 | 0 | 0 | 1 | 22 |
| 43 | 10 | 0 | 0 | 0 | 25 |
| | 20 | 0 | 0 | 0 | 10 |
| 46 | 10 | 0 | 0 | 0 | 54 |
| | 20 | 0 | 0 | 0 | 52 |
| 49 | 10 | 0 | 0 | 0 | 67 |
| | 20 | 1 | 0 | 1 | 38 |
| Non-treated plot | — | 0 | 0 | | 100 |

Note

*1: $\dfrac{\text{fresh weight in treated plot}}{\text{fresh weight in non-treated plot}} \times 100\%$

EXAMPLE 5

Herbicidal effect of the compounds indicated in the following table was investigated in a manner analogous to example 4.

Table 6

| Compound No. | Appln rate, g/are | Phytotoxicity | | | Relative *1 amount of crabgrass alive, % |
|---|---|---|---|---|---|
| | | Rice | Soya bean | Indian corn | |
| 51 | 10 | 0 | 0 | 0 | 18 |
| | 20 | 0 | 0 | 0 | 8 |
| 52 | 10 | 0 | 0 | 0 | 52 |
| | 20 | 0 | 0 | 0 | 36 |
| 54 | 10 | 0 | 0 | 0 | 13 |
| | 20 | 0 | 0 | 1 | 5 |
| 57 | 10 | 0 | 0 | 0 | 11 |
| | 20 | 0 | 0 | 0 | 8 |
| 59 | 10 | 0 | 0 | 0 | 33 |
| | 20 | 0 | 0 | 0 | 20 |
| 61 | 10 | 0 | 0 | 0 | 7 |

Table 6-continued

| Compound No. | Appln rate, g/are | Phytotoxicity Rice | Soya bean | Indian corn | Relative *1 amount of crabgrass alive, % |
|---|---|---|---|---|---|
| | 20 | 0 | 0 | 0 | 0 |
| 62 | 10 | 0 | 0 | 0 | '4 |
| | 20 | 0 | 0 | 1 | 0 |
| 66 | 10 | 0 | 0 | 0 | 63 |
| | 20 | 1 | 0 | 1 | 50 |
| Non-treated plot | — | 0 | 0 | 0 | 100 |

Note

*1: $\frac{\text{fresh weight in treated plot}}{\text{fresh weight in non-treated plot}} \times 100\%$

EXAMPLE 6

A quantity of paddy soil was placed in a Wagner pot of one five-thousandth are. A further quantity of soil mixed with biennial roots of slender spickrush (Eleocharis acicularis) and seeds of millet and toothcup (Rotala indica Koehne) was superimposed on the said paddy soil for transplanting paddy rice seedlings (four-leafed stage) therein. 5 days later, keeping the water 3 cm deep, the herbicidal compounds of the following table, formulated as wettable powder and diluted in water were applied in drops to the water surface of the pot. An application rate of 10 g and 20 g of compound per are was evaluated.

25 days after the treatment, the herbicidal effect of the compound was evaluated in the same manner as in example 1. The results are listed in the following table 7.

Table 7

| Compound No. | Appln rate, g/are | Herbicidal effect Millet | Toothcup | Slender spickrush | Phytotoxicity to rice |
|---|---|---|---|---|---|
| 37 | 10 | 4 | 4 | 2 | 0 |
| | 20 | 4 | 5 | 2 | 0 |
| 40 | 10 | 5 | 5 | 2 | 0 |
| | 20 | 5 | 5 | 3 | 0 |
| 43 | 10 | 5 | 5 | 3 | 0 |
| | 20 | 5 | 5 | 3 | 0 |
| 44 | 10 | 2 | 3 | 1 | 0 |
| | 20 | 3 | 4 | 2 | 0 |
| 47 | 10 | 3 | 3 | 1 | 0 |
| | 20 | 3 | 3 | 2 | 0 |
| 50 | 10 | 3 | 4 | 2 | 0 |
| | 20 | 4 | 4 | 3 | 0 |
| Non-treated plot | 0 | 0 | 0 | 0 | 0 |

EXAMPLE 7

The method of example 6 was followed to determine the herbicidal effect of the compounds numbered 53 to 65. The results are listed in the following table.

Table 8

| Compound No. | Appln rate, g/are | Herbicidal effect Millet | Toothcup | Slender spickrush | Phytotoxicity to rice |
|---|---|---|---|---|---|
| 53 | 10 | 3 | 4 | 1 | 0 |
| | 20 | 4 | 5 | 2 | 0 |
| 56 | 10 | 4 | 4 | 3 | 0 |
| | 20 | 5 | 5 | 3 | 0 |
| 58 | 10 | 4 | 5 | 3 | 0 |
| | 20 | 5 | 5 | 3 | 0 |
| 60 | 10 | 4 | 4 | 2 | 0 |
| | 20 | 4 | 5 | 3 | 0 |

Table 8-continued

| Compound No. | Appln rate, g/are | Herbicidal effect Millet | Toothcup | Slender spickrush | Phytotoxicity to rice |
|---|---|---|---|---|---|
| 62 | 10 | 5 | 5 | 3 | 0 |
| | 20 | 5 | 5 | 4 | 0 |
| 64 | 10 | 5 | 5 | 3 | 0 |
| | 20 | 5 | 5 | 4 | 0 |
| 65 | 10 | 5 | 5 | 2 | 0 |
| | 20 | 5 | 5 | 2 | 0 |
| Non-treated plot | — | 0 | 0 | 0 | 0 |

EXAMPLE 8

Beakers made of polyethylene were filled with upland field soil and seeded separately with millet, crabgrass, and radish. When the millet and crabgrass grew to the two- to three-leafed stage and the radish to the 1st leaf stage, the compounds of the following table, formulated as emulsions diluted with water were applied to the said plants in an amount of 10 l of the liquor per are. Concentrations of the active ingredient in the liquor of 0.25% and 0.5%, were evaluated respectively. 15 days after the treatment, the herbicidal effect was investigated in the same manner as described in example 3. The results are set forth in the following Table 9.

Table 9

| Compound No. | Concentration, % | Herbicidal effect Millet | Crabgrass | Radish |
|---|---|---|---|---|
| 38 | 0.25 | 3 | 4 | 4 |
| | 0.5 | 4 | 5 | 5 |
| 41 | 0.25 | 4 | 4 | 4 |
| | 0.5 | 4 | 5 | 5 |
| 45 | 0.25 | 3 | 3 | 4 |
| | 0.5 | 4 | 4 | 4 |
| 48 | 0.25 | 4 | 4 | 5 |
| | 0.5 | 5 | 5 | 5 |
| 49 | 0.25 | 4 | 4 | 4 |
| | 0.5 | 5 | 5 | 5 |
| Non-treated plot | — | 0 | 0 | 0 |

EXAMPLE 9

The same method as in example 8 was followed for determining the herbicidal effect of the compounds numbered 54 to 67 The results are listed in the following table 10

Table 10

| Compound No. | Concentration, % | Herbicidal effect Millet | Crabgrass | Radish |
|---|---|---|---|---|
| 54 | 0.25 | 3 | 4 | 5 |
| | 0.5 | 5 | 5 | 5 |
| 55 | 0.25 | 3 | 4 | 5 |
| | 0.5 | 5 | 5 | 5 |
| 57 | 0.25 | 2 | 3 | 4 |
| | 0.5 | 3 | 4 | 4 |
| 61 | 0.25 | 3 | 3 | 3 |
| | 0.5 | 3 | 4 | 4 |
| 63 | 0.25 | 5 | 5 | 5 |
| | 0.5 | 5 | 5 | 5 |
| 66 | 0.25 | 4 | 5 | 5 |
| | 0.5 | 5 | 5 | 5 |
| 67 | 0.25 | 2 | 2 | 3 |
| | 0.5 | 3 | 4 | 4 |
| Non-treated plot | — | 0 | 0 | 0 |

EXAMPLE 10

A upland field composed of Volcanic ash soil was seeded with soyabean. Immediately thereafter and before the sprouting of undesirable weeds, an aqueous suspension of wettable powder of compound No. 5 of table 1 was applied to the soil surface of the field. After 40 days standing, investigation was conducted with regard to the growth of undesirable weeds and the phytotoxicity of the compound to the soyabeam. For the sake of comparison, similar experiments were carried out, using Simazine.

Table 11

| Appln rate, g/are | Graminous g*1 | %*2 | Flatstage g*1 | %*2 | Broadleaf g*1 | %*2 | Total g*1 | %*2 | Phyto-toxicity to Soyabean |
|---|---|---|---|---|---|---|---|---|---|
| 5 | 97.7 | 26 | 2.0 | 80 | 10.6 | 56 | 110.3 | 28 | none |
| 10 | 74.0 | 20 | 1.7 | 68 | 4.3 | 23 | 80.8 | 21 | none |
| 15 | 56.0 | 15 | 2.0 | 80 | 3.4 | 18 | 61.8 | 16 | none |
| 20 | 6.6 | 1.8 | 0 | 0 | 0 | 0 | 6.6 | 1.6 | none |
| Simazine 7.5 | 105 | 28 | 2.3 | 92 | 10.6 | 56 | 118.1 | 30 | very slight |
| no treatment | 370.0 | 100 | 2.5 | 100 | 18.8 | 100 | 391.3 | 100 | none |

Note *1: Fresh weight of weed alive after treatment in g/sq.m.

*2: $\frac{\text{Fresh weight in treated plot}}{\text{Fresh weight in non-treated plot}} \times 100\%$

EXAMPLE 11

Paddy rice seedlings were transplanted in a paddy field of clay loam. 7 days later, when the weeds including graminous and broadleaf species were in the 1st-leaf stage, an aqueous suspension of wettable powder of compound No. 54 in table I-3 was applied to the soil of the paddy field. After 30 days standing in the natural state, the growth of and the chemical damage incurred by the paddy rice were investigated. For the sake of comparison, similar experiments were carried out with Nip.

Table 12

| Appln rate, g/are | Ratio of weeds alive *1 | | | | Phyto-toxicity to rice seedling |
|---|---|---|---|---|---|
| | Graminous, % | Flatstage, % | Broadleaf, % | Total, % | |
| 5 | 8.0 | 10.5 | 4.0 | 7.5 | none |
| 10 | 5.5 | 6.5 | 1.0 | 4.3 | none |
| 15 | 2.0 | 1.5 | 0 | 1.2 | none |
| Nip | | | | | |

Table 12-continued

| Appln rate, g/are | Ratio of weeds alive *1 | | | | Phyto-toxicity to rice seedling |
|---|---|---|---|---|---|
| | Graminous, % | Flatstage, % | Broadleaf, % | Total, % | |
| 21 | 7.5 | 8.0 | 6.0 | 7.2 | slight |
| 0 | 100 | 100 | 100 | 100 | none |

Note *1: $\frac{\text{Fresh weight in treated plot}}{\text{Fresh weight in non-treated plot}} \times 100\%$

We claim:

1. An N-substituted-$\Delta^1$-tetrahydrophthalimide represented by the formula

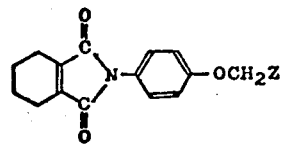

in which Z is phenyl, naphthyl or phenyl substituted by one or two substituents selected from halogen, nitro-, lower alkyl-, or lower alkoxy.

2. The compound as defined in claim 1 in which Z is 4-halophenyl.

3. The compound as defined in claim 1 in which Z is 4-alkyl phenyl.

4. The compound as defined in claim 2 in which 4-halophenyl is 4-chlorophenyl.

5. The compound as defined in claim 3 in which 4-alkylphenyl is 4-methylphenyl.

6. The compound as defined in claim 3 in which 4-alkylphenyl is 4-ethylphenyl.

* * * * *